United States Patent [19]
Nara et al.

[11] Patent Number: 4,536,405
[45] Date of Patent: Aug. 20, 1985

[54] MAKE-UP COSMETICS COMPOSITION

[75] Inventors: Michiko Nara, Tokyo; Kazunori Yamazaki, Kanagawa; Yasuko Akiyama, Tokyo, all of Japan

[73] Assignee: Shiseido Company Ltd., Tokyo, Japan

[21] Appl. No.: 75,762

[22] Filed: Sep. 17, 1979

Related U.S. Application Data

[63] Continuation of Ser. No. 891,778, Sep. 17, 1979, abandoned.

[30] Foreign Application Priority Data

Aug. 26, 1977 [JP] Japan ................. 52-102213

[51] Int. Cl.$^3$ .................. A61K 7/025; A61K 7/027; A61K 7/032; A61K 47/00
[52] U.S. Cl. .................... 514/781; 424/60; 424/61; 424/63; 424/64; 514/771
[58] Field of Search ............... 424/362, 63

[56] References Cited

U.S. PATENT DOCUMENTS

| | | | |
|---|---|---|---|
| 3,106,551 | 10/1963 | Lindenfors | 536/91 X |
| 3,646,214 | 2/1972 | Katz | 424/362 |
| 3,800,034 | 3/1974 | Kircher et al. | 424/63 |
| 3,818,105 | 6/1974 | Coopersmith et al. | 424/63 |
| 3,873,687 | 3/1975 | Demko | 424/63 |
| 3,877,955 | 4/1975 | Kalopessis et al. | 424/63 |
| 3,911,105 | 2/1976 | Papantoniou et al. | 424/63 |
| 3,937,811 | 2/1976 | Papantoniou et al. | 424/363 |
| 3,975,294 | 8/1976 | Dumoulin | 424/63 |

FOREIGN PATENT DOCUMENTS

| | | | |
|---|---|---|---|
| 606626 | 10/1960 | Canada | 536/11 |
| 2163864 | 7/1971 | Fed. Rep. of Germany | 424/362 |

OTHER PUBLICATIONS

Knectel, Amer. Perf. & Cosmetics, 10/1963, vol. 78, No. 10, pp. 95 to 97.

*Primary Examiner*—Dale R. Ore
*Attorney, Agent, or Firm*—Sughrue, Mion, Zinn, Macpeak & Seas

[57] ABSTRACT

A make-up cosmetic composition having good oil resistance, water resistance and adhesion, which contains at least one of (a) an organosoluble or a water- and organo-soluble ethyl hydroxyethyl cellulose and (b) an aromatic hydrocarbon resin having a softening point of at least about 120° C.

11 Claims, 1 Drawing Figure

| EVALUATION SCORE | 5 | 4 | 3 | 2 | 1 |
|---|---|---|---|---|---|
| OIL RESISTANCE | ○ | ◌ | ◍ | ◉ | ● |
| WATER RESISTANCE | ■ | ▦ | ▧ | ▨ | □ |
| ADHESION | ■ | ▦ | ▧ | ▨ | □ |

MAKE-UP COSMETICS COMPOSITION

This is a continuation, of application Ser. No. 891,778, filed Sept. 17, 1979, now abandoned.

BACKGROUND OF THE INVENTION

1. Field of the Invention

This invention relates to make-up cosmetics, especially eye make-up cosmetics.

2. Description of the Prior Art

Natural organosoluble resins such as shellac and rosin, organosoluble cellulose derivatives such as ethyl cellulose, nitrocellulose and cellulose acetate, alkyd resins, vinyl acetate resins, polyester resins, an arylsulfonamide-formaldehyde resin, water-soluble cellulose derivatives, and other various kinds of water-soluble polymers have been used as cosmetic ingredients. Organosoluble resins, however, have poor compatibility with other cosmetic ingredients except for some solvents, and therefore it is difficult to use such in cosmetics other than nail enamels. Good make-up maintenance is not possible with cosmetics containing such organosoluble resins.

For example, water-soluble cellulose derivatives such as sodium carboxymethyl cellulose, methyl cellulose and hydroxyethyl cellulose are available with various degrees of substitution and viscosities, and have long been used in many cosmetics, e.g., as described in Edward Sagarin *Cosmetics:Science and Technology,* Interscience Publishers, Inc., New York (1957).

On the other hand, very few organosoluble cellulose derivatives are soluble in ordinary aliphatic hydrocarbon oils (liquid paraffins with 15 to 20 carbon atoms, and squalane) or aliphatic hydrocarbon solvents having on the average 8.6 to 13.5 carbon atoms (e.g., isoparaffin), although some organosoluble cellulose derivatives, such as nitrocellulose, are soluble in nail enamel solvents (e.g., toluene, butyl acetate and ethyl acetate). Hence, almost no organosoluble cellulose derivatives have been employed in cosmetics other than nail enamels. The only prior application is found in *Cosmetics:-Science and Technology,* Second Edition, Wiley Interscience, John Wiley & Sons, New York (1972) which discloses the use of ethyl cellulose as a film-forming agent in a liquid lip rouge, and as a solidifying ingredient in a solid fragrance.

Conventional make-up cosmetics are available in various formulations such as water-based formulations, oil-based formulations, emulsion formulations and powder formulations. Of these formulations, powder make-up formulations have poor water resistance and oil resistance, and are susceptible to removal by the movement of the skin at the site of application and by rubbing of the site of application by the hands or clothing. In other words, these powdery cosmetics have poor adhesion to the skin, and tend to soil the clothing. Examples of water-based make-up formulations include, for example, an eyebrow make-up composed mainly of an aqueous emulsion of a synthetic resin such as a vinylidene chloride/vinyl chloride copolymer or a methyl methacrylate resin to which, it appears, some water resistance has been imparted to an extent such that it is not smeared by water (for example, as disclosed in Japanese Patent Application (OPI) No. 36347/73), and a liquid finishing make-up composition containing an aqueous ethanol solution and ethylene glycol or a soluble polymer such as a polyethylene glycol methacrylate or acrylate (for example, as described in Japanese Patent Publication No. 13973/1974). These water-based cosmetic formulations are susceptible to removal by perspiration, tears, rain, etc. In other words, they have poor water resistance and adhesion.

Emulsion cosmetic formulations can be classified as (a) aqueous emulsions (o/w type) comprising simply an oil and water, (b) emulsions obtained by adding a synthetic resin emulsion to (a), (c) oily emulsions (w/o type) comprising simply water and an oil, and (d) emulsions obtained by adding a synthetic resin emulsion to (c).

Emulsions of type (a) undoubtedly have poor water resistance and oil resistance.

Examples of emulsions of type (b) as make-up cosmetics are a make-up composition comprising polyvinyl acetate, polyvinyl butyrate, a vinyl chloride/vinyl acetate copolymer, or a polyacrylic acid ester (e.g., as described in British Pat. No. 1,110,240), and an eye liner composition comprising a stable aqueous dispersion of a water insoluble poly(acrylic acid ester) (e.g., as described in U.S. Pat. No. 3,639,572). Emulsions of this type are capable of withstanding normal use, but since these emulsions contain large amounts of hydrophilic substances, they tend to be removed by perspiration, tears, rain, etc. Such a cosmetic composition will be removed completely during swimming, for example. Furthermore, as described in the patents described above, these emulsions can be easily removed with cleansing creams or soap and water, therefore, it can be said that they have low water resistance.

Emulsions of type (c) include, for example, a creamy eye shadow containing an isoparaffinic hydrocarbon and large quantities of stearic acid and water [e.g., as disclosed in *American Cosmetics and Perfumery,* 87 (4), pages 41 to 44, (1972)], and cosmetics containing volatile isoparaffins having a boiling point ranging between about 160° and 200° C., especially those for eyelashes and eyebrows (e.g., as disclosed in Swiss Pat. No. 404,087). Emulsions of this type are susceptible to removal by sebum or oils of other cosmetics also used, and also by the movement of the skin at the site of application and rubbing of the site of application by the hands or clothing. In other words, these emulsions have poor oil resistance and adhesion and insufficient water resistance.

Emulsions of type (d) include, for example, make-up cosmetics containing acrylic polymers [e.g., as disclosed in *Parfumes Cosmetics Savons de France,* 3(3), pp. 149–160, (1973)], and eyelash cosmetics of the oily film type comprising a solid or semisolid wax or liquid oil, a volatile branched chain hydrocarbon and a synthetic resin emulsion (e.g., as disclosed in Japanese Patent Application (OPI) No. 125,044/1975). The make-up cosmetics containing acrylic polymers have poor water resistance and insufficient oil resistance. The eyelash cosmetics of the oily film type have insufficient water resistance and oil resistance. Thus, even emulsions of type (d) which are the best of the emulsion-type cosmetics have unsatisfactory water resistance and oil resistance.

Examples of oil formulations are liquid eyebrow paints comprising a stable mixture of an alkylbenzene, a polyamide resin and a fatty acid ester (e.g., as disclosed in Japanese Patent Publication No. 32680/1971). Since such paints contain large quantities of oleophilic substances, they are susceptible to removal by sebum or oils of other cosmetics also used, and also by the movement of the skin at the site of application or by rubbing the site of application by the hands or clothing. In other words, they have poor oil resistance and adhesion. Furthermore, since the viscosity of oily formulations changes with temperature, they are not stable.

Thus, conventional make-up cosmetics are susceptible to removal and have the disadvantage of poor make-up maintenance because they have low water resistance, oil resistance and adhesion to the site of application.

SUMMARY OF THE INVENTION

An object of this invention is to provide cosmetics having superior water resistance, oil resistance, and adhesion (resistance to rubbing).

A further object of this invention is to provide make-up cosmetics which are not removed by the action of body secretions such as perspiration, tears or sebum, by the action of water, whether due to the weather (rain, snow, etc.) or whether due to contact during activities such as swimming, and chemical actions, for example, the action of various ingredients of other cosmetics also used, and physical actions, for example, movement of the skin at the site of application of the cosmetics and rubbing of the site of application by the hands or clothing, and which do not soil the clothing.

An even further object of the present invention is to provide water-proof, smear-proof and rub-proof cosmetics.

The present invention provides a cosmetic composition comprising volatile liquid oils, waxes and pigments and containing at least one of (a) an organosoluble or an organo- and water-soluble ethyl hydroxyethyl cellulose and (b) an aromatic hydrocarbon resin having a softening point of at least about 120° C.

BRIEF DESCRIPTION OF THE ACCOMPANYING DRAWING

FIG. 1 shows simulations of standards used in evaluating oil resistance, water resistance and adhesion of a cosmetic as described hereinafter.

DETAILED DESCRIPTION OF THE INVENTION

The make-up cosmetics of this invention are free from the disadvantages of the prior art cosmetics described hereinbefore, and have resistance to removal under severe conditions.

Table 1 summarizes qualitative evaluations of various types of cosmetic formulations of the prior art in comparison with the make-up cosmetic of the present invention.

TABLE 1

| Type of Formulation | Stability | Water Resistance | Oil Resistance | Adhesion to Site of Application |
|---|---|---|---|---|
| Powder Formulation | O | X | X | X |
| Water Formulation | O | XΔ | O | Δ |
| Emulsion of Type (a) (o/w) | O | X | X | Δ |
| Emulsion of Type (b) [Type (a) + synthetic resin emulsion] | O | X | Δ | Δ |
| Emulsion of Type (c) (w/o) | O | Δ | X | Δ |
| Emulsion of Type (d)-1 [(c) + synthetic resin emulsion]* | Δ | X | Δ | O |
| Emulsion of Type (d)-2 [(c) +synthetic resin emulsion]** | O | O | Δ | O |
| Oil Formulation | X | O | X | Δ |
| Make-up Cosmetic of the Invention (oil, or oily emulsion) | O | O | O | O |

(Good O > Δ > XΔ > X Poor)
*, **: depending upon the composition, two Emulsion (d) types can be obtained.

Generally, make-up cosmetics contain liquid oil ingredients (volatile or non-volatile) such as isoparaffin (usually volatile), liquid paraffin (non-volatile), silicone (either volatile or non-volatile) or squalane, waxes such as bees wax, carnauba wax, ceresin or microcrystalline wax, pigments such as talc, titanium dioxide, iron oxides, ultramarine, or nacreous pigments, surface active agents such as saturated or unsaturated alkyl monoglycerides (e.g., stearyl monoglyceride), sorbitan fatty acid esters (e.g., sorbitan monopalmitate or sorbitan monostearate), polyoxyethylene sorbitan fatty acid esters (such as an addition product of 5 moles of polyoxyethylene with 1 mole of sorbitan monoleate) and/or organic quaternary ammonium salts (e.g., dimethyl distearyl ammonium chloride), resins such as petroleum resins, shellac or rosin, thickeners such as organic-modified montmorillonite, metal soaps such as aluminum stearate, perfumes, antiseptics such as a p-benzoic acid, fatty acid esters (the ester group containing 1 to 4 carbon atoms), water, co-solvent for, for example, ethyl hydroxyethyl cellulose such as alcohols (for example, ethanol and isopropyl alcohol), etc.

The make-up cosmetic of this invention is an oily or emulsion (w/o)-type make-up cosmetic containing the above-described ingredients, and additionally includes at least one of the above-described organosoluble or organo- and water-soluble cellulose derivatives (a) (ethyl hydroxyethyl cellulose which is referred to hereinbelow as "EHEC") and aromatic hydrocarbon resins having a high softening point (b). The make-up cosmetic of this invention possesses superior water resistance, oil resistance and adhesion, and has good make-up maintenance, which is not removed even under severe conditions such as during physical exercise such as swimming and various non-aquatic sports. The make-up cosmetic of this invention is especially suitable as eye make-up cosmetics.

The make-up cosmetics of this invention cannot be removed by soaps or water, and can be removed only using oil removers such as liquid paraffin, squalane, synthetic ester oils, and vegetable oils.

The EHEC used in this invention is a cellulose derivative in which many of the —OH groups in the cellulose units are substituted with ethoxy or ethoxyethyl groups as shown schematically below.

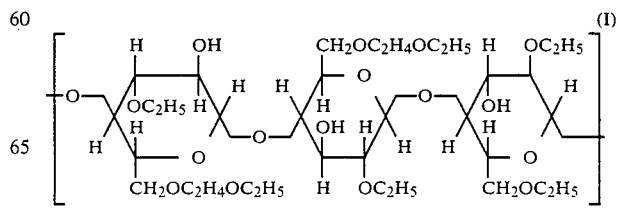

The degree of polymerization of the cellulose units in the EHEC is large enough for the EHEC to be film forming, generally about 50 to 3,000. The substitution in EHEC can occur at the —OH groups at various positions in the EHEC. EHEC is a mixed cellulose ether and can be prepared by a process involving the following three steps:

(1) Alkali cellulose formation in which cellulose is swollen by aqueous NaOH according to the following Cell—OH+NaOH⇌Cell—OH.NaOH where Cell represents cellulose.

(2) Hydroxyethylation, an alkali-catalyzed reaction which proceeds according to the following

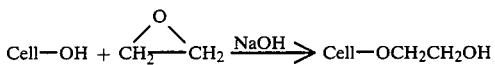

(3) Ethylation of hydroxyethyl cellulose which proceeds according to the following (a)
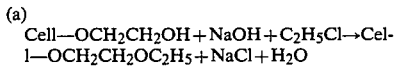
Cell—OCH$_2$CH$_2$OH+NaOH+C$_2$H$_5$Cl→Cell—OCH$_2$CH$_2$OC$_2$H$_5$+NaCl+H$_2$O in which the hydroxyethyl groups are ethylated, and (b)
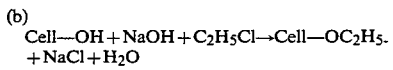
Cell—OH+NaOH+C$_2$H$_5$Cl→Cell—OC$_2$H$_5$+NaCl+H$_2$O in which the unsubstituted hydroxyl groups are ethylated.

The solubility of EHEC depends on the hydroxyethoxyl D.S. [reaction (2)] and ethoxyl D.S. [reaction (3)]. The hydroxyethoxyl b.S. of organo-soluble EHECs is about 0.3 to 0.9 and the ethoxyl D.S. is about 2.6 to 2.9. The ethoxyl D.S. of water- and organo-soluble EHEC, for example, MODOCOLL M. (disclosed in detail hereinafter) is 1.8 and the hydroxyethoxyl D.S. is 1.1. The degree of unsubstituted hydroxyl groups is 0.6. (The average number of hydroxyls in the anhydroglucose unit that are substituted in a particular product is defined as the degree of substitution (D.S.)) Ethylhydroxyethyl cellulose is manufactured by what is essentially a single-stage ethylation process. Alkali cellulose is prepared by steeping cellulose in aqueous sodium hydroxide and pressing to a sodium hydroxide to cellulose ratio of about 0.3:1 and a water to cellulose ratio of 1.1:1. The alkali cellulose is placed in an autoclave, air is removed, and ethyl chloride and ethylene oxide are added. The ethylene oxide is reacted at a temperature of 35° C. or less with the alkali cellulose and the ethyl chloride is then reacted at 110° C. or more and about 200 psi gauge pressure. The reaction efficiency is 50 to 60%. The products are washed with hot water and dried to granular products that are cold-water-soluble (as disclosed in *Encyclopedia of Polymer Science and Technology*, Vol. 3, p. 490. The method for production of organo-soluble EHEC is disclosed in U.S. Pat. No. 2,610,180).

EHEC is commercially available and examples of commercially available EHEC's that can be used in the present invention are "EHEC-LOW" (a trademark for an organosoluble EHEC made by Hercules Inc.) which has a viscosity of 20 to 35 centipoises [measured with a Brookfield viscometer (type L) at 25° C. as a 5% by weight toluene-ethanol (80:20 by weight) solution] and a density of 0.304 to 0.352 g/cm$^3$, and "MODOCOLL M" [a trademark for a organo- and water-soluble EHEC made by MoDoKemi AB (Sweden)] which has a viscosity of 12,500±2,500 centipoises [measured with a Brookfield viscometer (type LVT) at 20° C. as a 1.5% by weight methylene chloride-methanol (86:11 by weight) solution] and a density of 0.304 to 0.496 g/cm$^3$.

EHEC is compatible with polar waxes such as ester-type waxes (e.g., lanolin or beeswax) and oils such as castor oil or hexadecyl palmitate, and also dissolves or swells in non-polar aliphatic hydrocarbons having 6 to 20 carbon atoms. When EHEC is insoluble in these aliphatic hydrocarbons, a cosolvent such as methanol, ethanol, isopropanol or butanol can be added in an amount of about 1 to 10% by weight based on the weight of the aliphatic hydrocarbon to form a clear solution. The EHEC used in this invention dissolves in benzene, toluene, xylene, a chlorinated hydrocarbon such as methylene chloride or perchloroethylene, and CHClF$_2$ to an extent of up to 10% by weight to form a clear solution. Thus, EHEC has good compatibility with various materials. Other properties of EHEC are described in detail in "Hercules, EHEC", a catalog issued by Hercules Inc. In addition, EHEC as used in this invention serves to act as a thickener and as a separation inhibitor for pigments.

EHEC is incorporated into the make-up cosmetic base in an amount of about 1 to about 15% by weight, preferably 2 to 10% by weight, based on the total weight of the make-up cosmetic. If the amount of EHEC is less than about 1% by weight, satisfactory oil resistance, water resistance and adhesion is not obtained. If the amount of EHEC exceeds about 15% by weight, the compatibility of EHEC with the other ingredients tends to become poor, and the viscosity (or hardness) of the resulting composition as a cosmetic becomes too high.

In the present invention, organosoluble EHEC is especially suitable for use in oily cosmetics, and water- and organo-soluble EHEC is suitable for use in both oily cosmetics and emulsion (w/o type) cosmetics.

EHEC used in this invention has been found to be non-toxic and non-sensitizing as a result of safety testing for primary irritation on the skin, eye irritation, on acute oral toxicity testing and on closed human patch testing.

Suitable aromatic hydrocarbon resins having a high softening point which are used in this invention are resins which have good solubility in hydrocarbon solvents and have a softening point of at least about 120° C. The aromatic hydrocarbon resin is a thermoplastic resin obtained by polymerizing unsaturated hydrocarbons having a boiling point of about 120° to about 220° C. which are obtained by thermal cracking of petroleum. For example, the starting material for the resin can be prepared by thermally cracking petroleum, collecting the cracked oil fractions having a boiling point range between 120° and 220° C., preferably 140° to 220° C., and adjusting the components of the collected fractions such that the styrene content is not more than about 7% by weight based on the total weight of the fraction and not more than about 15% by weight based on the polymerizable components of all of the components, the total content of indene and alkyl derivatives thereof is at least about 5% by weight based on the total weight of the fraction, and the indene content based on the polymerizable components of all of the components is at least about 11% by weight. The hydrocarbon resin used in this invention is obtained, for example, by polymerizing this starting material together with about 0.05 to about 5% by weight, based on the starting material, of at least one phenol or alkylphenol in the presence of about 0.01 to about 5% by weight, based on the weight of the starting material, of a boron trifluoride-type catalyst (such as gaseous boron trifluoride, or a boron trifluoride-diethyl ether complex) at a temperature of about −30° C. to about +40° C. for a period of about 10 minutes to about 15 hours, decomposing and removing the catalyst, and separating the unreacted material and products of a low degree of polymerization by evaporation or distillation.

The aromatic hydrocarbon resin has a low bromine value of less than about 30, and has a light color. The aromatic hydrocarbon resin has an average molecular weight of about 1,000 to about 1,700. A preferred range of the average molecular weight is about 1,000 to about 1,500. Some commercially available hydrocarbon resins have a softening point of about 120° to about 180° C.

The method for producing the aromatic hydrocarbon resins which can be used in this invention set forth above is described in detail in Japanese Patent Publication No. 32432/1973 (which corresponds to U.S. Pat. No. 3,753,963).

The structure of the aromatic hydrocarbon resin described above, for example, can be represented by the following general formula (II)

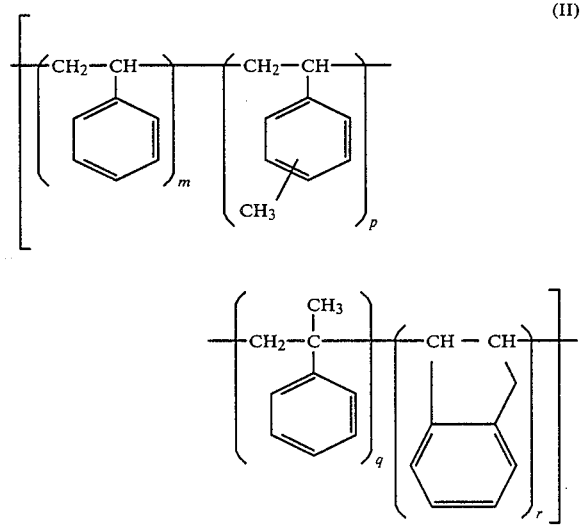

wherein m, p, q and r are positive integers. For example, an aromatic hydrocarbon resin of the above structure in which m, p, q and r are 1, 6, 1 and 2, respectively, and m+q, p and r are 2, 4 and 2, respectively, are commercially available. Commercially available hydrocarbon resins are, for example, Nisseki Neopolymers 120, 140 and 150 (trademarks for products of Nippon Oil Co., Ltd.).

The high-softening point aromatic hydrocarbon resin, as shown in Table 2 below, is one of a few resins which dissolve in the above-described liquid oils used for oily make-up cosmetics, and has good compatibility with other ingredients of make-up cosmetics, such as oils, waxes and other resins. Since the aromatic hydrocarbon resins has a higher softening point than other resins, a light yellow color and a slight odor, incorporation of such an aromatic hydrocarbon resin in make-up cosmetics does not adversely affect the color and smell of the make-up cosmetics and does not cause the cosmetics to be sticky. Thus, as shown in Table 3 below, make-up cosmetics having superior water resistance, oil resistance and adhesion can be obtained.

Application of the high-softening point aromatic hydrocarbon resins to paints, printing inks, adhesive agents and rubber tackifiers has heretofore been known, but no practical application of these resins to cosmetics prior to the present invention is known.

The objects of this invention can be achieved by incorporating this aromatic hydrocarbon resin in an amount of about 1 to about 15% by weight, preferably about 3 to about 10% by weight based on the weight of the make-up cosmetic. If the amount of this aromatic hydrocarbon resin is less than about 1% by weight, the oil resistance, water resistance and adhesion of the make-up cosmetic is not satisfactorily improved. If the amount of this aromatic hydrocarbon resin exceeds about 15% by weight, the solubility of the resin in the cosmetic tends to be insufficient, and the resulting composition sometimes has a viscosity (or hardness) exceeding the range suitable for cosmetics.

The aromatic hydrocarbon resins used in this invention meet the Japanese standards for food packaging materials as follows:

(1) Method for testing in Promulgation No. 434 of the Ministry of Health and Welfare, Japan 1966 (relating to the amount of formaldehyde which can be present).

(2) Method for Sanitary Testing established by the Japanese Pharmaceutical Society (relating to the amount of phthalic esters which can be present).

(3) Regulations in Nos. 385 and 442 of "Environment and Foods" (relating to the amount of polychlorinated biphenyls which can be present).

The aromatic hydrocarbon resins used in this invention have been found to be non-toxic as a result of safety testing for primary irritation on the skin, for eye irritation, and for acute oral toxicity test and on closed human patch testing.

Table 2 shows comparative data of the solubility in isoparaffin, a main ingredient of an oily cosmetic, of the high-softening aromatic hydrocarbon resins used in this invention and resins used in the prior art. In Table 2, resins Nos. 2, 3 and 4 are the aromatic hydrocarbon resins used in this invention. Each of the resins is used in a concentration of 10% by weight. The resin is added to isoparaffin, heated to 90° C. Then, the mixture is cooled to room temperature (25° C.), and the solubility of the resin is evaluated on the following scale.

O: Soluble
Δ: Slightly soluble
X: Practically insoluble

TABLE 2

| | | Solubility in Isoparaffin having on the Average 13.5 Carbon Atoms | | |
|---|---|---|---|---|
| No. | Trade Name | Type of Resin | Manufacturer | Solubility |
| 1 | Nisseki Neo-Polymer T | Aromatic Hydrocarbon Resin | Nippon Oil Co., Ltd. | O |

TABLE 2-continued

Solubility in Isoparaffin having on the Average 13.5 Carbon Atoms

| No. | Trade Name | Type of Resin | Manufacturer | Solubility |
|---|---|---|---|---|
| 2 | Nisseki Neo-Polymer 120 | High softening Point Aromatic Hydrocarbon Resin | Nippon Oil Co., Ltd. | O |
| 3 | Nisseki Neo-Polymer 140 | High softening Point Aromatic Hydrocarbon Resin | Nippon Oil Co., Ltd. | O |
| 4 | Nisseki Neo-Polymer 150 | High softening Point Aromatic Hydrocarbon Resin | Nippon Oil Co., Ltd. | O |
| 5 | Nisseki Neo-Polymer 160 | High softening Point Aromatic Hydrocarbon Resin | Nippon Oil Co., Ltd. | X |
| 6 | Hilac 111 | Ketone Resin | Hitachi Chemical Co., Ltd. | X |
| 7 | Aron KR | " | Toa Gosei Co., Ltd. | X |
| 8 | Beckosol EL 8011 | Alkyd Resin | Dainippon Ink and Chemicals, Inc. | O |
| 9 | Beckosol ODE-230-70 | " | Dainippon Ink and Chemicals, Inc. | X |
| 10 | Phthalkyd | " | Hitachi Chemical Co., Ltd. | X |
| 11 | Solid Beckosol No. 31 | Solid Alkyd Resin (A) | Dainippon Ink and Chemicals, Inc. | O |
| 12 | Solid Beckosol No. 96 | Solid Alkyd Resin (B) | Dainippon Ink and Chemicals, Inc. | O |
| 13 | Beckasite 1110 | Phenolic Resin Modified with a Natural Resin | Dainippon Ink and Chemicals, Inc. | X |
| 14 | Burnock TD-125 | Oil-modified Polyurethane | Dainippon Ink and Chemicals, Inc. | O |
| 15 | Neourethane Clear 700A | Urethane Resin | Tanabe Chemical Industries. | X |
| 16 | Melan 11 | Urea Resin | Hitachi Chemical | X |
| 17 | Melan 20 | Melamine Resin | " | |
| 18 | Burnock TD-91 | Polyisocyanate | Dainippon Ink and Chemicals, Inc. | X |
| 19 | Rosin (reagent) | Rosin | Kanto Chemical Co., Ltd. | O |
| 20 | Cellolyn 102 | Pentaerythritol Rosinate | Hercules | X |
| 21 | Hitanol 260 | Rosin-modified Phenol | Hitachi Chemical | X |
| 22 | Hitanol 40G | Rosin-modified Phenol | " | X |
| 23 | Hitalac 31G | Rosin-modified Maleic Acid | " | X |
| 24 | Hitalac 40G | Rosin-modified Maleic Acid | " | X |
| 25 | Hitalac 40M | Rosin-modified Maleic Acid | " | X |
| 26 | D.E.R. 330-J | Epoxy Resin | Dow Chemical | X |
| 27 | Epikote 828 | " | Shell Chemical | X |
| 28 | Epikote #1001 | " | " | X |
| 29 | Epicoaton P-400 Clear | " | Tanabe Chemical Industries | X |
| 30 | Burnock D-160 | Polyester | Dainippon Ink and Chemicals, Inc. | X |
| 31 | Daltosec 1150 | " | ICI | X |
| 32 | Daltosec 1250 | " | " | X |
| 33 | Estergum AA-1 | Ester Resin | Arakawa Rinsan Kagaku Kogyo K.K. | Δ |
| 34 | S-nyl P-18 | Vinyl Acetate Resin | Sekisui Kagaku Kogyo K.K. | X |
| 35 | S-nyl P-42 | Vinyl Acetate Resin | Sekisui Kagaku Kogyo K.K. | X |
| 36 | S-lec C | Vinyl Chloride/ Vinyl Acetate Resin | Sekisui Kagaku Kogyo K.K. | X |
| 37 | S-lec C-5 | Vinyl Chloride/ Vinyl Acetate Resin | Sekisui Kagaku Kogyo K.K. | X |
| 38 | S-lec MMS | Vinyl Chloride/ Vinyl Acetate/ Maleic Acid | Sekisui Kagaku Kogyo K.K. | X |

TABLE 2-continued

| No. | Trade Name | Solubility in Isoparaffin having on the Average 13.5 Carbon Atoms | | Solubility |
|---|---|---|---|---|
| | | Type of Resin | Manufacturer | |
| 39 | Resyn 28-1310 | Copolymer Vinyl Resin | National Starch | X |
| 40 | Resyn 28-2930 | " | " | X |
| 41 | Resyn 28-3307 | " | " | X |
| 42 | Gantrez AN119 | " | GAF | X |
| 43 | Gantrez AN139 | " | " | X |
| 44 | Gantrez AN169 | " | " | X |
| 45 | Gantrez ES225 | " | " | X |
| 46 | Gantrez ES-335-1 | " | " | X |
| 47 | Gantrez ES425 | " | " | X |
| 48 | Ganex V216 | Modified Polyvinyl Pyrrolidone (A) | Gokyo Sangyo K.K. | O |
| 49 | Ganex V220 | Modified Polyvinyl Pyrrolidone (B) | " | O |
| 50 | Epolen E-10 | Low-molecular-weight Polyethylene | Eastman Kodak | X |
| 51 | Epolen E-11 | Low-molecular-weight Polyethylene | " | X |
| 52 | Epolen E-12 | Low-molecular-weight Polyethylene | " | X |
| 53 | Epolen N-11 | Low-molecular-weight Polyethylene | " | Δ |
| 54 | Epolen N-12 | Low-molecular-weight Polyethylene | " | Δ |
| 55 | Pluscize L 53D | Acrylic Resin | Goo Kagaku Kogyo K.K. | X |
| 56 | Hitaloid 2405 | Acrylic Resin | Hitachi Chemical | X |
| 57 | Hitaloid 2606 | Acrylic Resin | " | X |
| 58 | Dry Transparent Whitelac | Shellac | " | X |
| 59 | Hitamide 415 | Polyamide | " | X |
| 60 | Hitamide 420 | " | " | X |
| 61 | Lackamide N-163-IM | " | Dainippon Ink and Chemicals | X |
| 62 | Lackamide N-164-L | " | Dainippon Ink and Chemicals | X |
| 63 | Versamid 230 | " | Daiichi General | X |
| 64 | Piccotex 100 | Polystyrene (A) | Exxon Corporation | O |
| 65 | Piccolastic A-75 | Polystyrene (B) | " | O |
| 66 | Piccolyte S-85 | Terpene Resin | " | Δ |
| 67 | Quintone A-100 | Terpene Resin (A) | Japanese Zeon Co., Ltd. | O |
| 68 | Quintone B-170 | Terpene Resin (B) | Japanese Zeon Co., Ltd. | O |
| 69 | Quintone C-100 Terpene Resin (C) | | Japanese Zeon Co., Ltd. | O |
| 70 | Quintone D-100 | Terpene Resin (D) | Japanese Zeon Co., Ltd. | O |
| 71 | Quintone U-185 | Terpene Resin (E) | Japanese Zeon Co., Ltd. | O |
| 72 | Polybutene 2000H | Polybutene | Idemitsu Oil Co., Ltd. | O |
| 73 | Vistanex LMMH | Polyisobutylene | Exxon Corporation | O |
| 74 | Escorez 1071U | Polyisoprene (A) | " | O |
| 75 | Escorez 1103U | Polyisoprene (B) | " | O |
| 76 | Hitanol 1131 | Alkylphenol | Hitachi Chemical | X |

Note
Resin No. 2 is the resin used in Example 3 given hereinafter.
Resin No. 3 is the resin used in Example 4 given hereinafter.
Resin No. 4 has a softening point of 155 ± 5° C. and an average molecular weight of about 1,500.

Those resins, in the above table, which have good solubility were formulated into cosmetics, and the cosmetics were evaluated for oil resistance, water resistance and adhesion.

The oil resistance, water resistance and adhesion were evaluated using the following methods.

(1) Oil Resistance 0.2 ml of an artificial sebum of the following composition was dropped onto a filter paper (4.5 × 3.0 cm) in a pan. Separately, a cosmetic of the following formulation was coated and dried (about 0.01 g/cm$^2$) on a round aluminum plate with a diameter of 2.3 cm. The aluminum plate was tapped on the filter paper thirty times with a force of 160 g/(2.3/2)$^2\pi$ so that the cosmetic coated surface contacted the filter paper. The transfer of the cosmetic onto the filter paper was evaluated. This operation can be performed, for example, using the device disclosed in Japanese Utility Model Application (OPI) No. 134383/77.

| Formulation of Artificial Sebum | |
|---|---|
| | (% by weight) |
| Squalane | 10 |
| Isostearyl Myristate | 20 |
| Olive Oil | 40 |
| Cholesterol | 2 |
| Palmitic Acid | 2 |
| Oleic Acid | 13 |
| Isostearic Acid | 13 |
| | 100 |

(2) Water Resistance

An artificial perspiration of the following formulation and 10 g of Duracon Pellets Type M90-12 (a trademark for polyacetal resin pellets, made by Polyplastics Corporation) (with an average diameter of 2 mm and a length of 3.5 mm) were placed in a cylindrical container having an inside diameter of 2.3 cm and a height of 5.3 cm. Separately, a cosmetic of the following formulation was coated and dried (0.01 g/cm$^2$) on a nylon plate (with a size of 1.5 cm×5.0 cm). The nylon plate was then placed in the cylindrical container and shaken for 2 hours with a KM Shaker (a shaker made by Iwaki K.K.; amplitude: 4 cm; number of oscillations; 330 times per minute) to mechanically rub the cosmetic coating with the Duracon Pellets. The peeling condition of the cosmetic coating was evaluated.

| Formulation of Artificial Perspiration | |
|---|---|
| | (% by weight) |
| Water | 99 |
| Sodium Chloride | 0.5 |
| Urea | 0.08 |
| Ammonia | 0.02 |
| Lactic Acid | 0.4 |
| | 100 |

(3) Adhesion

The same procedure as described in (2) above was performed except that the artificial perspiration was not used. Thus, the cosmetic coating was mechanically rubbed, and the peeling condition of the coating was evaluated.

| Cosmetic Formulation Used In Above Evaluations | |
|---|---|
| | (% by weight) |
| Black Iron Oxide | 25 |
| Wax | 15 |
| Resin (shown in Table 3 below) | 10 |
| Liquid Paraffin | 50 |

The results of these evaluations are shown in Table 3 below. The numerical values for the oil resistance, water resistance and adhesion shown in Table 3 are based on the rankings shown in the FIGURE. In the FIGURE, drawings for Oil Resistance are simulated appearances (amount) of the cosmetic transferred to the filter papers by tapping. Drawings for Water Resistance and Adhesion are simulated appearances (amount) of the cosmetic coated on the nylon plates after shaking. The Evaluation Score shows the degree of oil resistance, water resistance or adhesion using the following grades as shown below:

5 Excellent
4 Very Good
3 Good
2 Fair
1 Poor

TABLE 3

| Resin No. | Type of Resin | Oil Resistance | Water Resistance | Adhesion |
|---|---|---|---|---|
| 2 | High softening Point Aromatic Hydrocarbon Resin | 5 | 5 | 5 |
| 3 | High softening Point Aromatic Hydrocarbon Resin | 5 | 5 | 5 |
| 4 | High softening Point Aromatic Hydrocarbon Resin | 5 | 5 | 5 |
| 19 | Rosin | 4 | 5 | 5 |
| 11 | Solid Alkyd Resin | 3 | 5 | 5 |
| 64 | Polystyrene | 3 | 5 | 4 |
| 65 | " | 3 | 5 | 4 |
| 66 | Terpene Resin | 2 | 5 | 4 |
| 75 | Polyisoprene | 2 | 5 | 5 |
| 14 | Oil-modified Polyurethane | 2 | 5 | 5 |
| 67 | Terpene Resin | 1 | 5 | 5 |
| 68 | " | 2 | 5 | 5 |
| 69 | " | 1 | 5 | 5 |
| 79 | " | 2 | 5 | 5 |
| 71 | " | 2 | 5 | 5 |
| 71 | Polyisobutylene | 2 | 5 | 5 |
| 74 | Polyisoprene | 1 | 5 | 5 |
| 72 | Polybutene | 2 | 5 | 5 |
| 49 | Modified Polyvinylpyrrolidone | 1 | 5 | 2 |
| 48 | Modified Polyvinylpyrrolidone | 2 | 3 | 2 |

The same tests as above were performed using EHEC-LOW, and the results obtained are shown in Table 4 below.

TABLE 4

| Oil Resistance | Water Resistance | Adhesion |
|---|---|---|
| 5 | 5 | 5 |

As is clear from the results given in Tables 3 and 4 above, cosmetics containing the high-softening point aromatic hydrocarbon resin or EHEC have very good oil resistance, water resistance and adhesion.

Furthermore, the oil resistance, water resistance and adhesion of creamy mascaras of the formulation shown in Example 2 given hereinafter except that the amount of EHEC was varied from 0 (corresponding to a conventional cosmetic) to 2.5, 5.0, 10.0 and 15.0% by weight were evaluated. The evaluation methods used were the same as Methods (1), (2) and (3) above.

TABLE 4

| | Conventional Cosmetic | Make-up Cosmetic of the Invention | | | |
|---|---|---|---|---|---|
| Amount of EHEC (%) | 0 | 2.5 | 5.0 | 10.0 | 15.0 |
| Property | | | | | |

TABLE 4-continued

|  | Conventional Cosmetic | Make-up Cosmetic of the Invention | | | |
|---|---|---|---|---|---|
| Oil Resistance | 1 | 5 | 5 | 5 | 5 |
| Water Resistance | 1 | 3 | 3 | 5 | 5 |
| Adhesion | 1 | 3 | 5 | 5 | 5 |

From the results in Table 5 above, it can be seen that the make-up cosmetic of this invention as creamy mascaras have superior oil resistance, water resistance and adhesion.

Table 6 summarizes the oil resistance, water resistance and adhesion of creamy eyebrow make-ups of the formulation indicated in Example 3 given hereinafter except that the amount of the aromatic hydrocarbon resin was varied from 0 (corresponding to a conventional eyebrow make-up) to 2.5, 5.0, 10.0 and 15.0% by weight. The methods of evaluating the oil resistance, water resistance and adhesion are the same as Methods (1), (2) and (3) above.

TABLE 6

|  | Conventional Make-up | Make-up Cosmetic of the Invention | | | |
|---|---|---|---|---|---|
| Amount of Resin (%) | 0 | 2.5 | 5.0 | 10.0 | 15.0 |
| Property |  |  |  |  |  |
| Oil Resistance | 1 | 2 | 4 | 5 | 5 |
| Water Resistance | 1 | 2 | 3 | 4 | 5 |
| Adhesion | 1 | 2 | 4 | 5 | 5 |

From the results in Table 6, it can be seen that the make-up cosmetic of this invention as creamy eyebrow make-ups has superior oil resistance, water resistance and adhesion.

The oil resistance, water resistance and adhesion of the creamy foundation make-up of Example 4 given hereinafter and the various foundation make-ups (oily make-ups [1] and [2], emulsion, and water-base make-ups) shown below were evaluated. The results obtained are shown in Table 7 below. The test methods were the same as Methods (1), (2) and (3) above. The oil resistance was evaluated by using the artificial sebum described hereinabove, a suntan oil shown below, and squalane. The water resistance was evaluated using tap water, the artificial perspiration described above, and artificial salt water (3.5% aqueous solution of sodium chloride). The make-up of this invention was found to have good oil resistance, water resistance and adhesion as shown in Table 7.

| | (% by weight) |
|---|---|
| Oily Cosmetic [1] Formulation | |
| Ceresin | 5 |
| Microcrystalline Wax | 5 |
| Hexyldecyl Palmitate | 36.5 |
| Sorbitan Tristearate | 1.5 |
| Titanium Dioxide | 20 |
| Talc | 14 |
| Iron Oxides* | 17 |
| Perfume | 1.0 |
| The iron oxides comprised a mixture of | |
| Yellow Iron Oxide | 11.5 |
| Red Iron Oxide | 5.0 |
| Black Iron Oxide | 0.5 |
| | 17 |
| Oily Cosmetic [2] Formulation | |
| Liquid Paraffin | 28.5 |
| Lanolin | 10 |
| Microcrystalline Wax | 10 |
| Talc | 5 |
| Titanium Dioxide | 40 |
| Iron Oxides* | 5.0 |
| Sorbitan Monopalmitate | 1.0 |
| Perfume | 0.5 |
| The iron oxides comprised a mixture of | |
| Yellow Iron Oxide | 3.0 |
| Red Iron Oxide | 1.5 |
| Black Iron Oxide | 0.5 |
| | 5 |
| Emulsion-type Cosmetic Formulation | |
| Deodorized Cetanol | 1.0 |
| 1,3-Butylene Glycol | 10.0 |
| Stearic Acid | 2.0 |
| Isopropyl Myristate | 12.5 |
| Triethanolamine | 1.0 |
| Antiseptic (propyl p-hydroxybenzoate) | 0.30 |
| Mixed Pigment (*) | 20.0 |
| Magnesium Aluminum Stearate | 1.0 |
| Deionized Water | 49.2 |
| Perfume | 1.0 |
| Sorbitan Monoleate | 2.0 |
| *The mixed pigments comprised a mixture of the following | |
| Talc | 10.0 |
| Titanium Dioxide | 6.5 |
| Yellow Iron Oxide | 2.2 |
| Red Iron Oxide | 1.0 |
| Black Iron Oxide | 0.3 |
| | 20.0 |
| Water-base Cosmetic Formulation | |
| Squalane | 11.8 |
| Acetylated Lanolin | 10.0 |
| Polyoxyethylene Sorbitan Monooleate (average of 5 oxyethylene groups per molecule) | 1.0 |
| Stearic Acid | 2.0 |
| Triethanolamine | 1.0 |
| Talc | 55.0 |
| Titanium Dioxide | 15.0 |
| Mixed Iron Oxides* | 3.0 |
| Methyl p-Hydroxybenzoate | 0.2 |
| Perfume | 1.0 |
| *The iron oxides comprised a mixture of | |
| Yellow Iron Oxide | 2.0 |
| Red Iron Oxide | 0.8 |
| Black Iron Oxide | 0.2 |
| | 3.0 |
| Sun Tan Oil Formulation | |
| Liquid Paraffin | 59.94 |
| Olive Oil | 37 |
| Ultraviolet Absorber (ethyl p-hydroxyaminobenzoate) | 3 |
| Antioxidant ($\alpha$-tocopherol) | 0.01 |
| Perfume | 0.05 |
| | 100 |

TABLE 7

| | Oil Resistance | | | Water Resistance | | | |
|---|---|---|---|---|---|---|---|
| Cosmetic | Artificial Sebum | Sun Tan Oil | Squalane | Tap Water | Artificial Sweat | 3.5% NaCl Aqueous Solution | Adhesion |
| Example 4 | 4 | 3 | 5 | 5 | 5 | 5 | 5 |
| Oily Cosmetic [1] | 1 | 1 | 1 | 4 | 4 | 4 | 4 |
| Oily Cosmetic [2] | 1 | 1 | 1 | 1 | 1 | 1 | 2 |
| Emulsion-type Cosmetic | 2 | 2 | 2 | 1 | 1 | 1 | 1 |
| Water-base | 2 | 1 | 1 | — | 2 | — | 2 |

TABLE 7-continued

| | Oil Resistance | | | Water Resistance 3.5% | | |
|---|---|---|---|---|---|---|
| Cosmetic | Artificial Sebum | Sun Tan Oil | Squalane | Tap Water | Artificial Sweat | NaCl Aqueous Solution | Adhesion |
| Cosmetic | | | | | | | |

EHEC and the aromatic hydrocarbon resin having a high softening point can be used together if desired. The total amount of the EHEC and the aromatic hydrocarbon resin can be about 1 to about 15% by weight of the total weight of the make-up cosmetic. Various amounts can be selected depending on the desired products by considering the film-forming property of EHEC and the adhesiveness of the aromatic hydrocarbon resin.

Both the EHEC and the aromatic hydrocarbon resin have excellent properties for improving the water resistance and the oil resistance of cosmetics. EHEC is superior as a film forming agent and on the other hand, the aromatic hydrocarbon resin is superior as an adhesive, especially. EHEC tends to cause the cosmetic film to have a low degree of plasticity, thereby the cosmetic film becomes crispy and have a poor feeling when worn. The aromatic hydrocarbon tends to cause the cosmetic be thickened. Therefore, a cosmetic, especially an eyeliner, has a shortcoming when applied to the skin in a thin film. However, when EHEC and the aromatic hydrocarbon resin are used in combination, the shortcomings of both the EHEC and the aromatic hydrocarbon can be overcome.

The following Examples are given to further illustrate the present invention in greater detail. Unless otherwise specified, all percentages, parts, ratios and the like are by weight.

EXAMPLE 1

A make-up cosmetic of this invention in the form of an eye shadow having the following formulation was prepared as described below.

| | % by weight |
|---|---|
| Isoparaffin | 59.75 |
| Acetylated Lanolin | 5 |
| Ceresin | 10 |
| EHEC-LOW | 5 |
| Beeswax | 5 |
| Nacreous Pigment | 10 |
| Ultramarine Blue | 5 |
| Antiseptic (methyl p-hydroxybenzoate) | 0.05 |
| Perfume | 0.2 |

The acetylated lanolin, ceresin and beeswax were uniformly heated at 80° to 90° C. to melt them and a mixture of the isoparaffin and EHEC was added. The mixture was stirred and dispersed. Then, the nacreous pigment, ultramarine blue, the antiseptic, and the perfume were added to form a blue creamy eyeshadow.

EXAMPLE 2

A make-up cosmetic of this invention in the form of a creamy mascara make-up having the following formulation was prepared as described below.

| | % by weight |
|---|---|
| Isoparaffin | 50 |
| Beeswax | 13 |
| Carnauba Wax | 3 |
| EHEC-LOW | 10 |
| Acetylated Lanolin | 5 |
| Sorbitan Monostearate | 2 |
| Deionized Water | 14.8 |
| Carbon Black | 2 |
| Antiseptic (methyl p-hydroxybenzoate) | 0.1 |
| Perfume | 0.1 |

The beeswax, carnauba wax, acetylated lanolin and sorbitan monostearate were heated uniformly at 80° to 90° C. to dissolve, and a solution of EHEC dissolved in isoparaffin at 70° C. was added. The mixture was stirred and dispersed. Then, carbon black was added, and deionized water, the antiseptic and perfume were added to form a black creamy mascara make-up.

EXAMPLE 3

A make-up cosmetic of this invention in the form of a creamy eyebrow make-up having the following formulation was prepared as described below.

| | % by weight |
|---|---|
| Isoparaffin | 40 |
| Ceresin Wax | 10 |
| Aromatic Hydrocarbon Resin* | 15 |
| Stearyl Monoglyceride | 3 |
| Aluminum Stearate | 1 |
| Deionized Water | 14.6 |
| Black Iron Oxide | 3 |
| Kaolin | 13 |
| Antiseptic (propyl p-hydroxybenzoate) | 0.2 |
| Perfume | 0.2 |

*Nisseki Neopolymer 120 (a product of Nippon Oil K.K.; an aromatic hydrocarbon resin having a softening point of 120 ± 5° C., and an average molecular weight of about 1,000).

The aromatic hydrocarbon resin, ceresin wax, stearyl monoglyceride and aluminum stearate were added to isoparaffin, and the mixture was heated at 80° to 90° C. and dispersed. The pigment, water, propyl p-hydroxybenzoate and perfume were added and dispersed with stirring. The mixture was then cooled to form a creamy eyebrow make-up.

EXAMPLE 4

A make-up cosmetic of this invention in the form of a creamy foundation make-up having the following formulation was prepared as described below.

| | % by weight |
|---|---|
| Isoparaffin | 42.6 |
| Microcrystalline Wax | 5 |
| Acetylated Lanolin | 5 |
| EHEC-LOW | 5 |
| Aromatic Hydrocarbon Resin* | 5 |
| Sorbitan Monopalmitate | 3 |
| Iron Oxide (brown) | 3.5 |
| Titanium Dioxide | 10 |
| Talc | 16.5 |
| Organic-modified Montmorillonite (Quaternium-18 Bentonite) | 2 |
| Antiseptic (methyl p-hydroxybenzoate) | 0.1 |
| Ethanol (95%) | 2 |

| | % by weight |
|---|---|
| Perfume | 0.3 |

*Nisseki Neopolymer 140 (a trademark for a highsoftening aromatic hydrocarbon resin having a softening point of 145 ± 5° C. and an average molecular weight of about 1,400).

The EHEC, the aromatic hydrocarbon resin, the microcrystalline wax, sorbitan monopalmitate and the organic-modified montmorillonite were added to the isoparaffin and heated at 80° to 90° C. and dispersed. Then, the pigment, the methyl p-hydroxybenzoate and the perfume were added, and the mixture was dispersed with stirring, and cooled.

The cosmetic ingredients described in the formulations given above other than the EHEC and the aromatic hydrocarbon resin are merely illustrative and are not to be construed as limiting. Other ingredients usually employed in cosmetics can be used in this invention.

The make-up cosmetic of the present invention can be broadly applied to other foundations, eye make-up cosmetics such as eyebrow paints, eyeshadows, eyeliners and mascaras, and skin and hair cosmetics such as body paints, nail enamels, lip rouges, hair colorants and leg make-up cosmetics.

While the invention has been described in detail and with reference to specific embodiments thereof, it will be apparent to one skilled in the art that various changes and modifications can be made therein without departing from the spirit and scope thereof.

What is claimed is:

1. A make-up cosmetic composition containing one or more volatile liquid oils, waxes and pigments and further at least one of (a) an organo-soluble ethyl hydroxyethyl cellulose having a hydroxy ethoxyl degree of substitution of about 0.3 to 0.9 and an ethoxyl degree of substitution of about 2.6 to 2.9, and (b) an aromatic hydrocarbon resin having a softening point of at least about 120° C. said aromatic hydrocarbon resin being represented by the following formula (II)

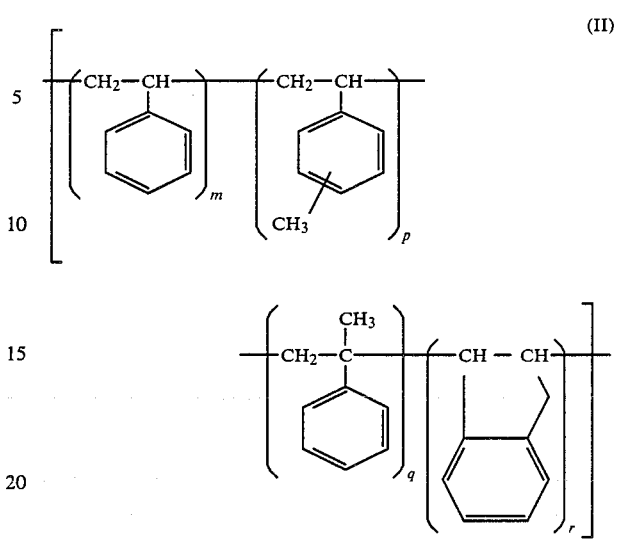

wherein m, p, q and r are positive integers.

2. The cosmetic composition of claim 1, wherein the amount of said at least one of the ethyl hydroxyethyl cellulose (a) and the aromatic hydrocarbon resin (b) is about 1 to about 15% by weight based on the total weight of the cosmetic composition.

3. The cosmetic composition of claim 1, which is an oily cosmetic.

4. The cosmetic composition of claim 1, which is a water-in-oil type emulsion.

5. The cosmetic composition of claim 1, wherein the ethyl hydroxyethyl cellulose (a) is a cellulose derivative in which the hydroxyl groups at various positions of the cellulose units are substituted with ethoxy or ethoxyethyl groups.

6. The cosmetic composition of claim 1, wherein the ethyl hydroxyethyl cellulose (a) has a viscosity of about 20 to 35 centipoises as measured at 25° C. as a 5% by weight toluene-ethanol solution in which the weight ratio of toluene to ethanol is 80:20 and has a density of 0.304 to 0.352 g/cm$^3$.

7. The cosmetic composition of claim 1, comprising oily cosmetic ingredients and the ethyl hydroxyethyl cellulose (a) is an organosoluble ethyl hydroxyethyl cellulose.

8. The cosmetic composition of claim 1, wherein the aromatic hydrocarbon resin (b) has an average molecular weight of about 1,000 to about 1,700.

9. The cosmetic composition of claim 1, wherein the aromatic hydrocarbon resin (b) has a softening point in the range of about 120° to about 180° C.

10. The cosmetic composition of claim 1, containing both the organosoluble ethyl hydroxyethyl cellulose (a) and the aromatic hydrocarbon resin (b).

11. The cosmetic composition of claim 10, wherein the total amount of the ethyl hydroxyethyl cellulose (a) and the aromatic hydrocarbon resin (b) is about 1 to about 15% by weight based on the total weight of the cosmetic composition.

* * * * *